US011950877B2

(12) United States Patent
Meyer et al.

(10) Patent No.: US 11,950,877 B2
(45) Date of Patent: Apr. 9, 2024

(54) SYSTEM AND METHOD FOR FULLY AUTOMATIC LV SEGMENTATION OF MYOCARDIAL FIRST-PASS PERFUSION IMAGES

(71) Applicant: UNIVERSITY OF VIRGINIA PATENT FOUNDATION, Charlottesville, VA (US)

(72) Inventors: Craig H. Meyer, Charlottesville, VA (US); Xue Feng, Charlottesville, VA (US); Michael Salerno, Charlottesville, VA (US)

(73) Assignee: UNIVERSITY OF VIRGINIA PATENT FOUNDATION, Charlottesville, VA (US)

( * ) Notice: Subject to any disclaimer, the term of this patent is extended or adjusted under 35 U.S.C. 154(b) by 407 days.

(21) Appl. No.: 17/428,832

(22) PCT Filed: Feb. 5, 2020

(86) PCT No.: PCT/US2020/016892
§ 371 (c)(1),
(2) Date: Aug. 5, 2021

(87) PCT Pub. No.: WO2020/163539
PCT Pub. Date: Aug. 13, 2020

(65) Prior Publication Data
US 2022/0125314 A1 Apr. 28, 2022

Related U.S. Application Data

(60) Provisional application No. 62/801,329, filed on Feb. 5, 2019.

(51) Int. Cl.
*A61B 5/00* (2006.01)
*A61B 5/026* (2006.01)
(Continued)

(52) U.S. Cl.
CPC .......... *A61B 5/0044* (2013.01); *A61B 5/0263* (2013.01); *A61B 5/055* (2013.01);
(Continued)

(58) Field of Classification Search
CPC ..... A61B 5/0044; A61B 5/0263; A61B 5/055; A61B 5/7267; A61B 2576/023;
(Continued)

(56) References Cited

U.S. PATENT DOCUMENTS 7,725,165 B2* 5/2010 Chen ...................... A61B 90/36
382/128
10,366,488 B2* 7/2019 Nakano ................. A61B 6/037
(Continued)

OTHER PUBLICATIONS

International Search Report and Written Opinion, issued in PCT/US2020/016892, dated May 12, 2020, 10 pages.
(Continued)

*Primary Examiner* — Michael S Osinski
(74) *Attorney, Agent, or Firm* — Meunier Carlin & Curfman LLC

(57) ABSTRACT

A computerized system and method of modeling myocardial tissue perfusion can include acquiring a plurality of original frames of magnetic resonance imaging (MRI) data representing images of a heart of a subject and developing a manually segmented set of ground truth frames from the original frames. Applying training augmentation techniques to a training set of the originals frame of MRI data can prepare the data for training at least one convolutional neural network (CNN). The CNN can segment the training set of frames according to the ground truth frames. Applying the respective input test frames to a trained CNN can allow for segmenting an endocardium layer and an epicardium layer within the respective images of the input test frames. The segmented images can be used in calculating myocardial
(Continued)

blood flow into the myocardium from segmented images of the input test frames.

23 Claims, 10 Drawing Sheets

(51) Int. Cl.
| | |
|---|---|
| A61B 5/055 | (2006.01) |
| G01R 33/483 | (2006.01) |
| G01R 33/563 | (2006.01) |
| G06N 3/08 | (2023.01) |
| G06T 3/00 | (2006.01) |
| G06T 3/60 | (2006.01) |
| G06T 7/00 | (2017.01) |
| G06T 7/11 | (2017.01) |
| G06T 7/143 | (2017.01) |
| G06T 7/149 | (2017.01) |
| G06T 7/194 | (2017.01) |
| G06T 7/215 | (2017.01) |
| G06T 7/33 | (2017.01) |
| G16H 30/40 | (2018.01) |

(52) U.S. Cl.
CPC ........ *A61B 5/7267* (2013.01); *G01R 33/4835* (2013.01); *G01R 33/56366* (2013.01); *G06N 3/08* (2013.01); *G06T 3/0006* (2013.01); *G06T 3/60* (2013.01); *G06T 7/0014* (2013.01); *G06T 7/11* (2017.01); *G06T 7/143* (2017.01); *G06T 7/149* (2017.01); *G06T 7/194* (2017.01); *G06T 7/215* (2017.01); *G06T 7/33* (2017.01); *G16H 30/40* (2018.01); *A61B 2576/023* (2013.01); *G06T 2207/10088* (2013.01); *G06T 2207/20081* (2013.01); *G06T 2207/20084* (2013.01); *G06T 2207/30048* (2013.01); *G06T 2207/30104* (2013.01); *G06T 2207/30168* (2013.01)

(58) Field of Classification Search
CPC .......... G01R 33/4835; G01R 33/56366; G01R 33/243; G01R 33/4824; G01R 33/5602; G01R 33/5607; G01R 33/5608; G06N 3/08; G06N 3/045; G06N 3/084; G06N 3/088; G06T 3/0006; G06T 3/60; G06T 7/0014; G06T 7/11; G06T 7/143; G06T 7/149; G06T 7/194; G06T 7/215; G06T 7/33; G06T 2207/10088; G06T 2207/20081; G06T 2207/20084; G06T 2207/30048; G06T 2207/30104; G06T 2207/30168; G06T 7/0012; G06T 2207/10081; G06T 2207/30016; G06T 2207/30101; G16H 30/40; G16H 50/20; G16H 30/20; G16H 50/30; G06V 10/82; G06V 10/454; G06V 10/764; G06V 2201/03
See application file for complete search history.

(56) References Cited

U.S. PATENT DOCUMENTS

| | | | | |
|---|---|---|---|---|
| 10,726,545 | B2* | 7/2020 | Marrouche | A61B 5/7207 |
| 2005/0113680 | A1* | 5/2005 | Ikeda | G06T 7/0012 |
| | | | | 128/920 |
| 2007/0270689 | A1* | 11/2007 | Lothert | A61B 6/032 |
| | | | | 600/428 |
| 2010/0249592 | A1 | 9/2010 | Langeland et al. | |
| 2012/0245453 | A1* | 9/2012 | Tryggestad | A61B 6/5288 |
| | | | | 600/407 |
| 2014/0148693 | A1 | 5/2014 | Taylor | |
| 2015/0265228 | A1* | 9/2015 | Kyriakou | A61B 5/14553 |
| | | | | 600/431 |
| 2017/0049379 | A1* | 2/2017 | Luo | G01R 33/4833 |
| 2018/0012365 | A1* | 1/2018 | Chefd'hotel | G06T 7/12 |
| 2018/0150528 | A1 | 5/2018 | Shah et al. | |
| 2018/0259608 | A1 | 9/2018 | Golden et al. | |
| 2019/0046068 | A1* | 2/2019 | Ceccaldi | G06V 10/764 |
| 2019/0205606 | A1* | 7/2019 | Zhou | G06V 10/454 |
| 2019/0279416 | A1* | 9/2019 | Lee | G06T 19/20 |
| 2019/0311478 | A1* | 10/2019 | Avendi | G06V 30/274 |
| 2020/0167930 | A1* | 5/2020 | Wang | G06N 3/08 |
| 2020/0211188 | A1* | 7/2020 | Gao | G06N 3/08 |
| 2020/0311877 | A1* | 10/2020 | S | G06T 7/194 |
| 2020/0311913 | A1* | 10/2020 | Soni | G06V 10/7784 |
| 2021/0000449 | A1* | 1/2021 | Deo | G06N 3/08 |
| 2021/0106314 | A1* | 4/2021 | Aladahalli | G06V 10/26 |
| 2021/0233252 | A1* | 7/2021 | Paul | G06T 7/30 |
| 2021/0335041 | A1* | 10/2021 | Haslam | G16H 50/50 |
| 2021/0342629 | A1* | 11/2021 | Hu | G06F 18/253 |
| 2021/0406591 | A1* | 12/2021 | Luo | G06T 11/00 |
| 2022/0104884 | A1* | 4/2022 | Leiderman | A61B 1/000095 |
| 2022/0125314 | A1* | 4/2022 | Meyer | G01R 33/4835 |
| 2022/0133284 | A1* | 5/2022 | Lampotang | A61B 34/20 |
| | | | | 600/562 |
| 2022/0156522 | A1* | 5/2022 | Shechtman | G06N 3/088 |
| 2022/0198667 | A1* | 6/2022 | Zhao | G06V 10/267 |
| 2022/0208355 | A1* | 6/2022 | Li | G06T 7/0016 |
| 2022/0284583 | A1* | 9/2022 | Lee | G16H 30/20 |
| 2022/0327815 | A1* | 10/2022 | Picon Ruiz | G06T 7/001 |
| 2022/0335611 | A1* | 10/2022 | Seong | A61B 6/501 |
| 2022/0386987 | A1* | 12/2022 | Camps | A61B 5/1135 |
| 2023/0045882 | A1* | 2/2023 | Yamamoto | G16H 50/20 |
| 2023/0145439 | A1* | 5/2023 | Suk | G06Q 30/0601 |
| | | | | 705/44 |
| 2023/0157657 | A1* | 5/2023 | Takahashi | A61B 6/487 |
| | | | | 378/1 |
| 2023/0169155 | A1* | 6/2023 | Vuppala | H04N 1/00843 |
| | | | | 348/207.11 |
| 2023/0172451 | A1* | 6/2023 | Seo | A61B 5/02014 |
| | | | | 382/128 |
| 2023/0222654 | A1* | 7/2023 | Fan | G06V 10/82 |
| | | | | 382/128 |

OTHER PUBLICATIONS

Tran. "A Fully Convolutional Neural Network for Cardiac Segmentation in Short-Axis MRI." In: Cornell University Library/ Computer Science/Computer Vision and Pattern Recognition, Apr. 27, 2017, [online] [retrieved on Apr. 14, 2020 (Apr. 14, 2020)] Retrieved from the Internet< URL: https://arxiv.org/abs/1604.00494 >.

Ronneberger et al. "U-Net: Convolutional Networks for Biomedical Image Segmentation." In: Cornell University Library/Computer Science/Computer Vision and Pattern Recognition, May 18, 2015, [online] [retrieved on Apr. 14, 2020 (Apr. 14, 2020)] Retrieved from the Internet< URL: https://arxiv.org/abs/1505.04597 >.

* cited by examiner

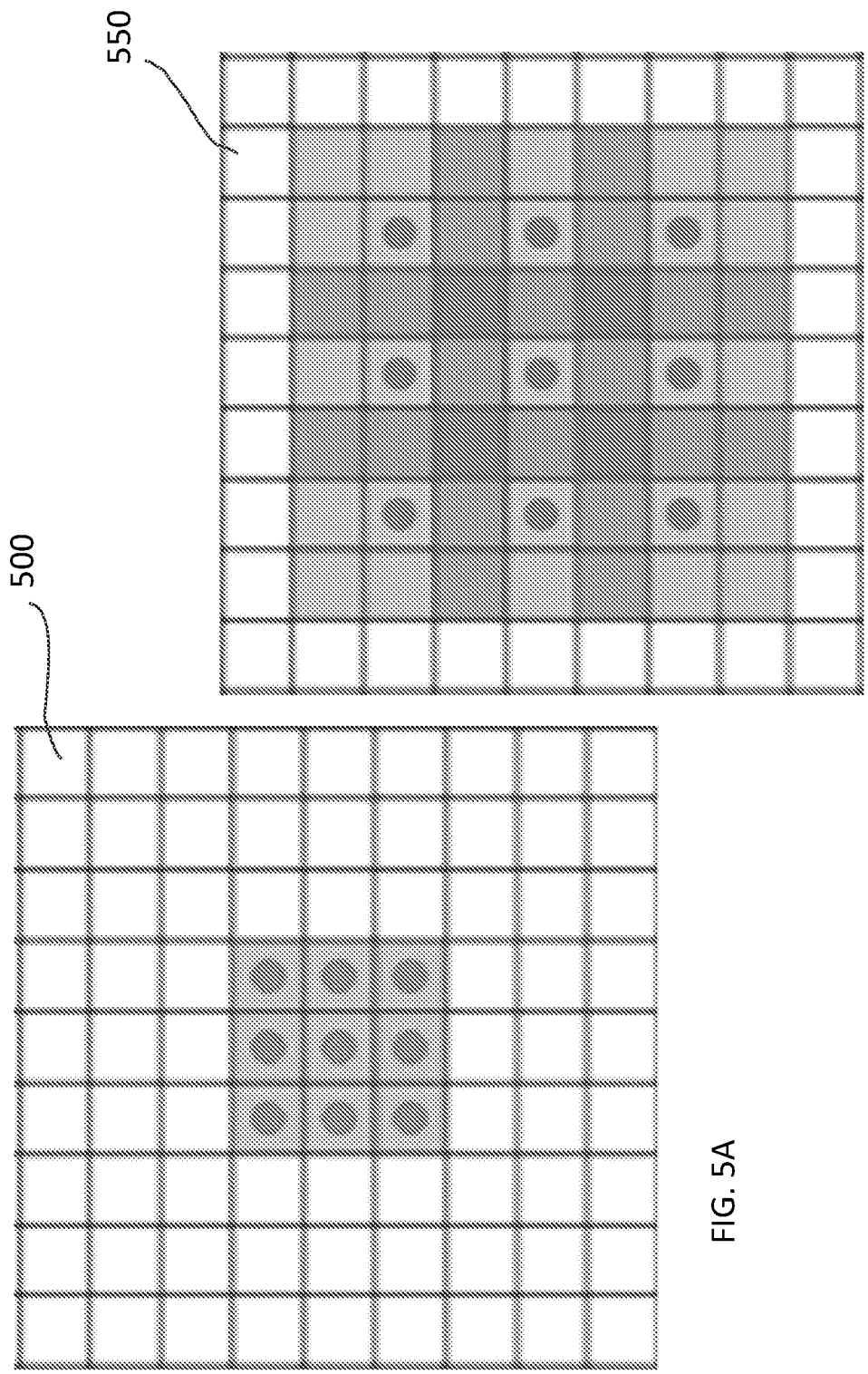

SYSTEM AND METHOD FOR FULLY AUTOMATIC LV SEGMENTATION OF MYOCARDIAL FIRST-PASS PERFUSION IMAGES

CROSS-REFERENCE TO RELATED APPLICATION

This is a national phase application filed under 35 U.S.C § 371 of PCT/US2020/016892, filed on Feb. 5, 2020, entitled "SYSTEM AND METHOD FOR FULLY AUTOMATIC LV SEGMENTATION OF MYOCARDIAL FIRST-PASS PERFUSION IMAGES," which claims priority to and benefit under 35 U.S.C § 119(e) of U.S. Provisional Patent Application Ser. No. 62/801,329 entitled "System and Method for Fully Automatic LV Segmentation of Myocardial First-Pass Perfusion Images" filed Feb. 5, 2019, both of which are hereby incorporated by reference herein in their entirety as if fully set forth below.

STATEMENT OF GOVERNMENT INTEREST

This invention was made with government support under Grant No. HL131919 awarded by The National Institutes of Health. The government has certain rights in the invention.

FIELD

This disclosure relates to magnetic resonance imaging (MRI) operations that develop and validate a deep convolutional neural network (DCNN) method for automatic left ventricle (LV) segmentation of perfusion images.

BACKGROUND

The present disclosure generally relates to the field of medical imaging for analysis of certain physiological activities of a subject. Various conventional imaging techniques can provide for an assessment of a subject, such as a patient's heart with regard to spatial coverage. For example, two-dimensional (2D) and three-dimensional (3D) measurements can provide a complete assessment of the heart with regard to spatial coverage and a comprehensive evaluation of physical conditions that aid in the assessment of heart disease.

It is known in the art that epicardial and endocardial segmentation of the left ventricle (LV) is required to calculate pixel-wise myocardial blood flow. Manual segmentation is often performed on a single frame assuming minimal respiratory and cardiac motion among frames. Accurate automatic segmentation on all frames can improve the quantification accuracy and robustness against motion as the accuracy of pixel-to-pixel correspondence across frames can be improved. Challenges in segmentation include significantly varied image contrast at different frames and very poor contrast before contrast arrival. Deep convolutional neural network (DCNN) segmentation is a promising tool to achieve good segmentation quality. These techniques can be used with numerous data acquisition procedures that allow for MRI data to be analyzed in various domains, such as studying heart tissue qualities with cine data.

SUMMARY

In some aspects, the present disclosure relates to systems and methods of modeling myocardial tissue perfusion which, in some embodiments, include acquiring a plurality of original frames of magnetic resonance imaging (MRI) data representing images of a heart of a subject and developing a manually segmented set of ground truth frames from the original frames. Applying training augmentation techniques to a training set of the originals frame of MM data prepares the data for training at least one convolutional neural network (CNN). The CNN segments the training set of frames according to the ground truth frames. A trained CNN is used for testing, with the CNN, a set of test images from the plurality of original frames. Applying the respective input test frames to a trained CNN allows for segmenting an endocardium layer and an epicardium layer within the respective images of the input test frames. The segmented images may be used in calculating myocardial blood flow into the myocardium from segmented images of the input test frames.

Other aspects and features according to the example embodiments of the disclosed technology will become apparent to those of ordinary skill in the art, upon reviewing the following detailed description in conjunction with the accompanying figures.

BRIEF DESCRIPTION OF THE DRAWINGS

Reference will now be made to the accompanying drawings, which are not necessarily drawn to scale.

FIG. 5A is a first frame of pixel data acquired by Mill procedures as set forth herein.

FIG. 5B is a second frame of pixel data that represents a dilated frame version of the frame of date in FIG. 5A and used according to the disclosure herein.

DETAILED DESCRIPTION

Figure 1:
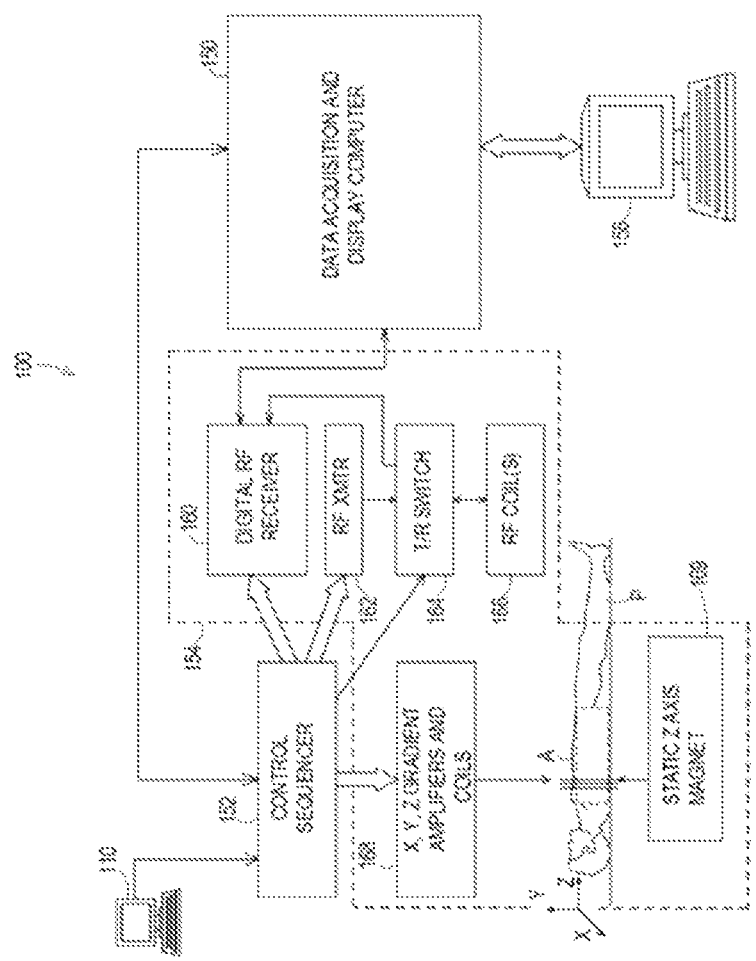
FIG. 1 is a system diagram illustrating an operating environment capable of implementing aspects of the present disclosure.

Although example embodiments of the disclosed technology are explained in detail herein, it is to be understood that other embodiments are contemplated. Accordingly, it is not intended that the disclosed technology be limited in its scope to the details of construction and arrangement of components set forth in the following description or illustrated in the drawings. The disclosed technology is capable of other embodiments and of being practiced or carried out in various ways.

It must also be noted that, as used in the specification and the appended claims, the singular forms "a," "an" and "the" include plural referents unless the context clearly dictates otherwise. Ranges may be expressed herein as from "about" or "approximately" one particular value and/or to "about" or "approximately" another particular value. When such a range is expressed, other exemplary embodiments include from the one particular value and/or to the other particular value.

By "comprising" or "containing" or "including" is meant that at least the named compound, element, particle, or method step is present in the composition or article or method, but does not exclude the presence of other compounds, materials, particles, method steps, even if the other such compounds, material, particles, method steps have the same function as what is named.

In describing example embodiments, terminology will be resorted to for the sake of clarity. It is intended that each term contemplates its broadest meaning as understood by those skilled in the art and includes all technical equivalents that operate in a similar manner to accomplish a similar purpose. It is also to be understood that the mention of one or more steps of a method does not preclude the presence of additional method steps or intervening method steps between those steps expressly identified. Steps of a method may be performed in a different order than those described herein without departing from the scope of the disclosed technology. Similarly, it is also to be understood that the mention of one or more components in a device or system does not preclude the presence of additional components or intervening components between those components expressly identified.

As discussed herein, a "subject" (or "patient") may be any applicable human, animal, or other organism, living or dead, or other biological or molecular structure or chemical environment, and may relate to particular components of the subject, for instance specific organs, tissues, or fluids of a subject, may be in a particular location of the subject, referred to herein as an "area of interest" or a "region of interest."

Some references, which may include various patents, patent applications, and publications, are cited in a reference list and discussed in the disclosure provided herein. The citation and/or discussion of such references is provided merely to clarify the description of the disclosed technology and is not an admission that any such reference is "prior art" to any aspects of the disclosed technology described herein. All references cited and discussed in this specification are incorporated herein by reference in their entireties and to the same extent as if each reference was individually incorporated by reference.

In the following description, references are made to the accompanying drawings that form a part hereof and that show, by way of illustration, specific embodiments or examples. In referring to the drawings, like numerals represent like elements throughout the several figures.

FIG. 1 is a system diagram illustrating an operating environment capable of implementing aspects of the present disclosure in accordance with one or more example embodiments. FIG. 1 illustrates an example of a magnetic resonance imaging (Mill) system 100, including a data acquisition and display computer 150 coupled to an operator console 110, an MM real-time control sequencer 152, and an Mill subsystem 154. The Mill subsystem 154 may include XYZ magnetic gradient coils and associated amplifiers 168, a static Z-axis magnet 169, a digital RF transmitter 162, a digital RF receiver 160, a transmit/receive switch 164, and RF coil(s) 166. The MM subsystem 154 may be controlled in real time by control sequencer 152 to generate magnetic and radio frequency fields that stimulate magnetic resonance phenomena in a living subject, patient P, to be imaged. A contrast-enhanced image of an area of interest A of the patient P may be shown on display 158. The display 158 may be implemented through a variety of output interfaces, including a monitor, printer, or data storage.

The area of interest "A" corresponds to a region associated with one or more physiological activities in patient "P". The area of interest shown in the example embodiment of FIG. 1 corresponds to a chest region of patient "P", but the area of interest for purposes of implementing aspects of the disclosure presented herein is not limited to the chest area. It should be recognized and appreciated that the area of interest can be one or more of a brain region, heart region, and upper or lower limb regions of the patient "P", for example.

It should be appreciated that any number and type of computer-based medical imaging systems or components, including various types of commercially available medical imaging systems and components, may be used to practice certain aspects of the present disclosure. Systems as described herein with respect to example embodiments are not intended to be specifically limited to magnetic resonance imaging (Mill) implementations or the particular system shown in FIG. 1.

One or more data acquisition or data collection steps as described herein in accordance with one or more embodiments may include acquiring, collecting, receiving, or otherwise obtaining data such as imaging data corresponding to an area of interest. By way of example, data acquisition or collection may include acquiring data via a data acquisition device, receiving data from an on-site or off-site data acquisition device or from another data collection, storage, or processing device. Similarly, data acquisition or data collection devices of a system in accordance with one or more embodiments of the present disclosure may include any device configured to acquire, collect, or otherwise obtain data, or to receive data from a data acquisition device within the system, an independent data acquisition device located on-site or off-site, or another data collection, storage, or processing device.

Figure 2:
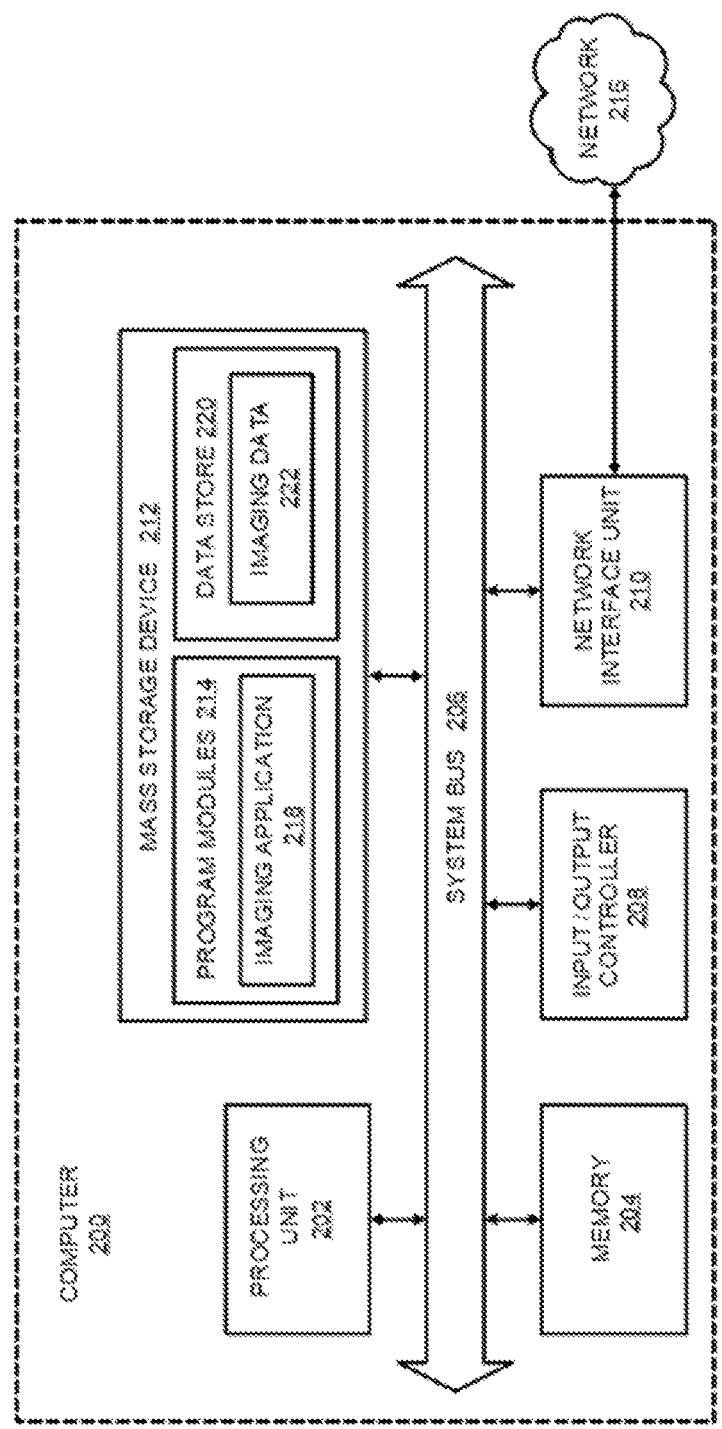
FIG. 2 is a computer architecture diagram showing a general computing system capable of implementing aspects of the present disclosure.
Figure 3:
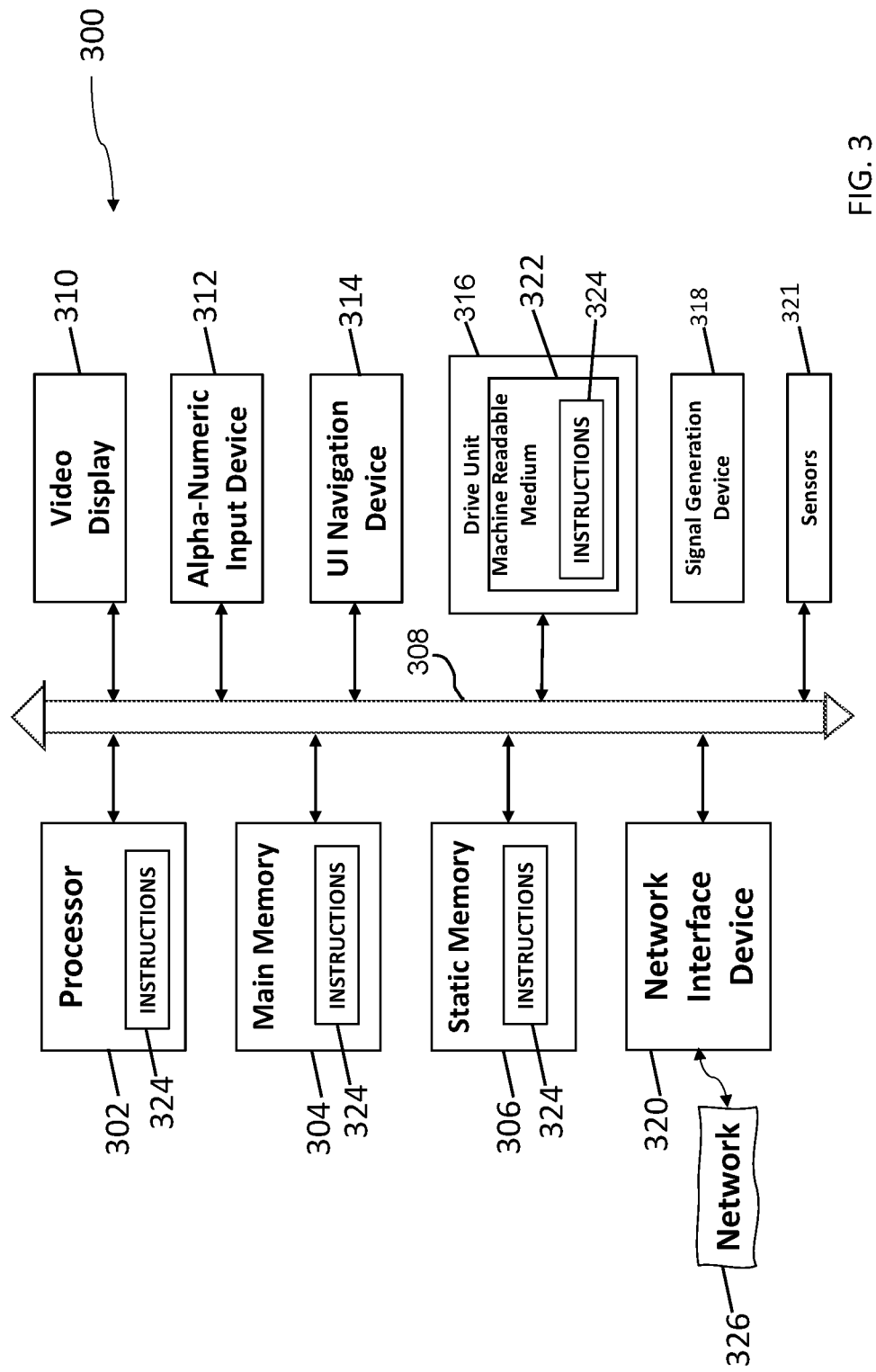
FIG. 3 is a network diagram illustrating how data acquired and processed by the systems and methods of this disclosure may be transmitted and received remotely.

FIG. 2 is a computer architecture diagram showing a general computing system capable of implementing aspects of the present disclosure in accordance with one or more embodiments described herein. A computer 200 may be configured to perform one or more functions associated with embodiments of this disclosure. For example, the computer 200 may be configured to perform operations of the method as described below. It should be appreciated that the computer 200 may be implemented within a single computing device or a computing system formed with multiple connected computing devices. The computer 200 may be configured to perform various distributed computing tasks, which may distribute processing and/or storage resources among the multiple devices. The data acquisition and display computer 150 and/or operator console 110 of the system shown in FIG. 1 may include one or more systems and components of the computer 200.

As shown, the computer 200 includes a processing unit 202 ("CPU"), a system memory 204, and a system bus 206 that couples the memory 204 to the CPU 202. The computer 200 further includes a mass storage device 212 for storing program modules 214. The program modules 214 may be operable to perform one or more functions associated with embodiments of method as illustrated in one or more of the figures of this disclosure, for example to cause the computer 200 to perform operations of the present disclosure as described below. The program modules 214 may include an imaging application 218 for performing data acquisition functions as described herein, for example to receive image data corresponding to magnetic resonance imaging of an area of interest. The computer 200 can include a data store 220 for storing data that may include imaging-related data 222 such as acquired image data, and a modeling data store 224 for storing image modeling data, or other various types of data utilized in practicing aspects of the present disclosure.

The mass storage device 212 is connected to the CPU 202 through a mass storage controller (not shown) connected to the bus 206. The mass storage device 212 and its associated computer-storage media provide non-volatile storage for the computer 200. Although the description of computer-storage media contained herein refers to a mass storage device, such as a hard disk or CD-ROM drive, it should be appreciated by those skilled in the art that computer-storage media can be any available computer storage media that can be accessed by the computer 200.

By way of example, and not limitation, computer-storage media (also referred to herein as a "computer-readable storage medium" or "computer-readable storage media") may include volatile and non-volatile, removable and non-removable media implemented in any method or technology for storage of information such as computer-storage instructions, data structures, program modules, or other data. For example, computer storage media includes, but is not limited to, RAM, ROM, EPROM, EEPROM, flash memory or other solid state memory technology, CD-ROM, digital versatile disks ("DVD"), HD-DVD, BLU-RAY, or other optical storage, magnetic cassettes, magnetic tape, magnetic disk storage or other magnetic storage devices, or any other medium which can be used to store the desired information and which can be accessed by the computer 200. Transitory signals are not "computer-storage media", "computer-readable storage medium" or "computer-readable storage media" as described herein.

According to various embodiments, the computer 200 may operate in a networked environment using connections to other local or remote computers through a network 216 via a network interface unit 210 connected to the bus 206. The network interface unit 210 may facilitate connection of the computing device inputs and outputs to one or more suitable networks and/or connections such as a local area network (LAN), a wide area network (WAN), the Internet, a cellular network, a radio frequency network, a Bluetooth-enabled network, a Wi-Fi enabled network, a satellite-based network, or other wired and/or wireless networks for communication with external devices and/or systems. The computer 200 may also include an input/output controller 208 for receiving and processing input from a number of input devices. Input devices may include one or more of keyboards, mice, stylus, touchscreens, microphones, audio capturing devices, or image/video capturing devices. An end user may utilize such input devices to interact with a user interface, for example a graphical user interface, for managing various functions performed by the computer 200.

The bus 206 may enable the processing unit 202 to read code and/or data to/from the mass storage device 212 or other computer-storage media. The computer-storage media may represent apparatus in the form of storage elements that are implemented using any suitable technology, including but not limited to semiconductors, magnetic materials, optics, or the like. The computer-storage media may represent memory components, whether characterized as RAM, ROM, flash, or other types of technology. The computer-storage media may also represent secondary storage, whether implemented as hard drives or otherwise. Hard drive implementations may be characterized as solid state or may include rotating media storing magnetically-encoded information. The program modules 214, which include the imaging application 218, may include instructions that, when loaded into the processing unit 202 and executed, cause the computer 200 to provide functions associated with embodiments illustrated herein. The program modules 214 may also provide various tools or techniques by which the computer 200 may participate within the overall systems or operating environments using the components, flows, and data structures discussed throughout this description.

In general, the program modules 214 may, when loaded into the processing unit 202 and executed, transform the processing unit 202 and the overall computer 200 from a general-purpose computing system into a special-purpose computing system. The processing unit 202 may be constructed from any number of transistors or other discrete circuit elements, which may individually or collectively assume any number of states. More specifically, the processing unit 202 may operate as a finite-state machine, in response to executable instructions contained within the program modules 214. These computer-executable instructions may transform the processing unit 202 by specifying how the processing unit 202 transitions between states, thereby transforming the transistors or other discrete hardware elements constituting the processing unit 202.

Encoding the program modules 214 may also transform the physical structure of the computer-storage media. The specific transformation of physical structure may depend on various factors, in different implementations of this description. Examples of such factors may include but are not limited to the technology used to implement the computer-storage media, whether the computer storage media are characterized as primary or secondary storage, and the like. For example, if the computer-storage media are implemented as semiconductor-based memory, the program modules 214 may transform the physical state of the semiconductor memory, when the software is encoded therein. For example, the program modules 214 may transform the state of transistors, capacitors, or other discrete circuit elements constituting the semiconductor memory.

As another example, the computer-storage media may be implemented using magnetic or optical technology. In such implementations, the program modules 214 may transform the physical state of magnetic or optical media, when the software is encoded therein. These transformations may include altering the magnetic characteristics of particular locations within given magnetic media. These transformations may also include altering the physical features or characteristics of particular locations within given optical media, to change the optical characteristics of those locations. Other transformations of physical media are possible without departing from the scope of the present description, with the foregoing examples provided only to facilitate this discussion.

The computing system can include clients and servers. A client and server are generally remote from each other and generally interact through a communication network. The relationship of client and server arises by virtue of computer programs running on the respective computers and having a client-server relationship to each other. In embodiments deploying a programmable computing system, it will be appreciated that both hardware and software architectures require consideration. Specifically, it will be appreciated that the choice of whether to implement certain functionality in permanently configured hardware (e.g., an ASIC), in temporarily configured hardware (e.g., a combination of software and a programmable processor), or a combination of permanently and temporarily configured hardware can be a design choice. Below are set out hardware (e.g., machine 300) and software architectures that can be deployed in example embodiments.

The machine 300 can operate as a standalone device or the machine 300 can be connected (e.g., networked) to other machines. In a networked deployment, the machine 300 can operate in the capacity of either a server or a client machine in server-client network environments. In an example, machine 300 can act as a peer machine in peer-to-peer (or other distributed) network environments. The machine 300 can be a personal computer (PC), a tablet PC, a set-top box (STB), a Personal Digital Assistant (PDA), a mobile telephone, a web appliance, a network router, switch or bridge, or any machine capable of executing instructions (sequential or otherwise) specifying actions to be taken (e.g., performed) by the machine 300. Further, while only a single machine 300 is illustrated, the term "machine" shall also be taken to include any collection of machines that individually or jointly execute a set (or multiple sets) of instructions to perform any one or more of the methodologies discussed herein.

Example machine (e.g., computer system) 300 can include a processor 302 (e.g., a central processing unit (CPU), a graphics processing unit (GPU) or both), a main memory 304 and a static memory 306, some or all of which can communicate with each other via a bus 308. The machine 300 can further include a display unit 310, an alphanumeric input device 312 (e.g., a keyboard), and a user interface (UI) navigation device 311 (e.g., a mouse). In an example, the display unit 810, input device 317 and UI navigation device 314 can be a touch screen display. The machine 300 can additionally include a storage device (e.g., drive unit) 316, a signal generation device 318 (e.g., a speaker), a network interface device 320, and one or more sensors 321, such as a global positioning system (GPS) sensor, compass, accelerometer, or other sensor. The storage device 316 can include a machine readable medium 322 on which is stored one or more sets of data structures or instructions 324 (e.g., software) embodying or utilized by any one or more of the methodologies or functions described herein. The instructions 324 can also reside, completely or at least partially, within the main memory 304, within static memory 306, or within the processor 302 during execution thereof by the machine 300. In an example, one or any combination of the processor 302, the main memory 304, the static memory 306, or the storage device 316 can constitute machine readable media. While the machine readable medium 322 is illustrated as a single medium, the term "machine readable medium" can include a single medium or multiple media (e.g., a centralized or distributed database, and/or associated caches and servers) that configured to store the one or more instructions 324. The term "machine readable medium" can also be taken to include any tangible medium that is capable of storing, encoding, or carrying instructions for execution by the machine and that cause the machine to perform any one or more of the methodologies of the present disclosure or that is capable of storing, encoding or carrying data structures utilized by or associated with such instructions. The term "machine readable medium" can accordingly be taken to include, but not be limited to, solid-state memories, and optical and magnetic media.

Specific examples of machine readable media can include non-volatile memory, including, by way of example, semiconductor memory devices (e.g., Electrically Programmable Read-Only Memory (EPROM), Electrically Erasable Programmable Read-Only Memory (EEPROM)) and flash memory devices; magnetic disks such as internal hard disks and removable disks; magnetooptical disks; and CD-ROM and DVD-ROM disks. The instructions 324 can further be transmitted or received over a communications network 326 using a transmission medium via the network interface device 320 utilizing any one of a number of transfer protocols (e.g., frame relay, IP, TCP, UDP, HTTP, etc.). Example communication networks can include a local area network (LAN), a wide area network (WAN), a packet data network (e.g., the Internet), mobile telephone networks (e.g., cellular networks), Plain Old Telephone (POTS) networks, and wireless data networks (e.g., IEEE 802.11 standards family known as Wi-Fi®, IEEE 802.16 standards family known as Wi Max®), peer-to-peer (P2P) networks, among others. The term "transmission medium" shall be taken to include any intangible medium that is capable of storing, encoding or carrying instructions for execution by the machine, and includes digital or analog communications signals or other intangible medium to facilitate communication of such software.

This disclosure introduces a Convolutional Neural Network approach to suppress artifact-generating signals in Stimulated Echo MRI. As set forth herein, Cine Displacement Encoding with Stimulated Echoes (DENSE), as one non-limiting instance of stimulated MM, provides an accurate and reproducible measure of tissue displacement. DENSE takes the advantage of a phase memory property of stimulated echoes and encodes the displacement information into the phase stimulated echoes. During the DENSE acquisitions, another signal due to the T1-relaxation of magnetization is acquired which generates artifacts and should be suppressed as shown in the figures.

Figure 4:
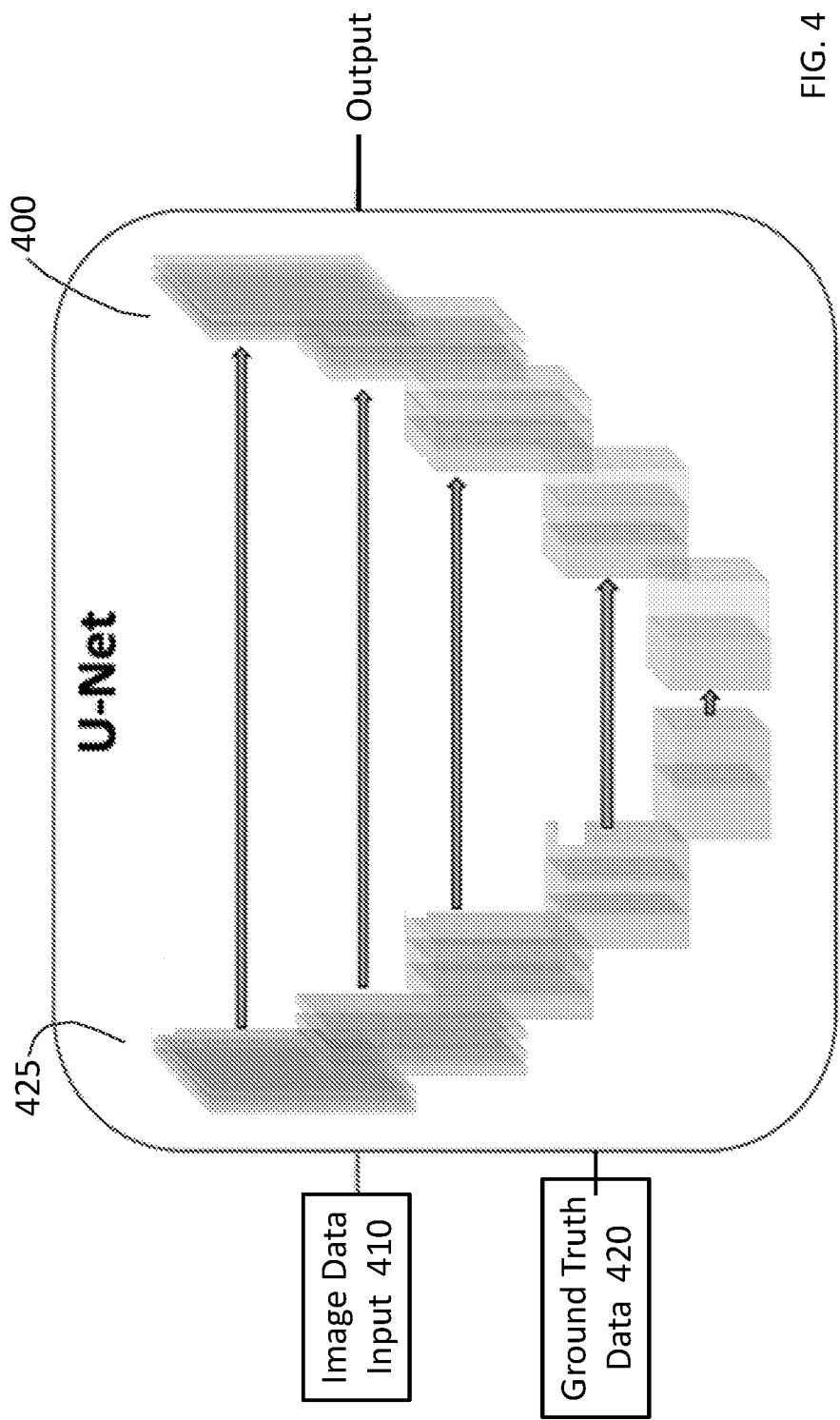
FIG. 4 is an illustration of a U-NET convolutional neural network according to the present disclosure.

Instead of requiring multiple acquisition steps, this disclosure presents an alternative approach using a convolutional neural network (CNN) 400, illustrated in FIG. 4, to suppress the artifact-generating echo. In one non-limiting example, a U-Net, shown by example in FIG. 4, is trained using phase-cycled artifact-free images established, via additive and subtraction image processing, as ground truth frames. Phase cycling techniques used to produce MRI images with suppressed artifacts have been disclosed in at least U.S. patent application Ser. No. 16/368,218 (Cai), published as United States Patent Publication No. 2019/0302211 and incorporated by reference herein. DENSE images, taken from a single acquisition, having both stimulated (STE) and T1-relaxation echoes therein. The CNN 400 is trained to generate artifact-free images in the output. This avoids the additional data acquisition and shortens the scan time in DENSE MRI.

In one example shown herein, to train the U-Net 400, the single acquisition DENSE data was used as the image data input 410 and the phase-cycled, artifact-free data was used as ground-truth comparison frames 420. Many aspects of this disclosure are based upon a non-limiting example in which MRI data includes the features noted below and segmented according to a deep convolutional neural network (DCNN). In one implementation, that does not limit the disclosure, the DCNN 400 is a U-Net backbone with the following optionally included design choices, which may change for the use at hand and still be within the scope of this disclosure.

The slice dimension of input images for the CNN is two dimensional (2D), which is chosen to enhance output accuracy in light of limited and unreliable slice continuity.

The temporal dimension of input images may be chosen as single frame inputs to improve robustness against frame-to-frame motion.

The loss function used to train the network may, in non-limiting embodiments, include soft Dice loss and weighted cross entropy, among other error value calculations.

The system may use dilated convolutions instead of regular convolutions to increase the receptive field without introducing more parameters.

The batch size=1 with layer normalization in which pre-processing steps include normalizing over each feature map.

In certain non-limiting aspects of this disclosure, the of encoding and decoding layers in the CNN is four, and the number of features at the first level is 64.

Figure 6B:
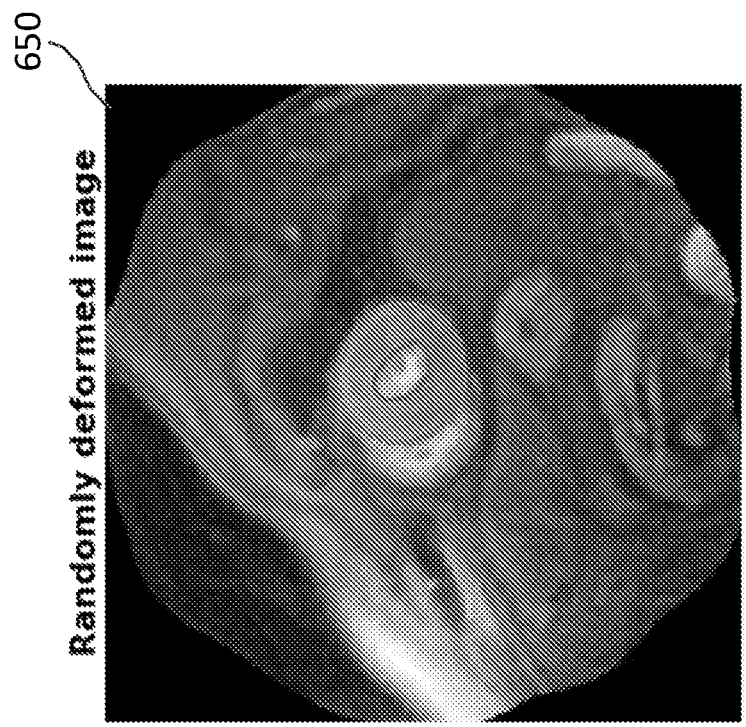
FIG. 6B is a pre-processed frame of image data subject to augmentation techniques described herein.
Figure 6A:
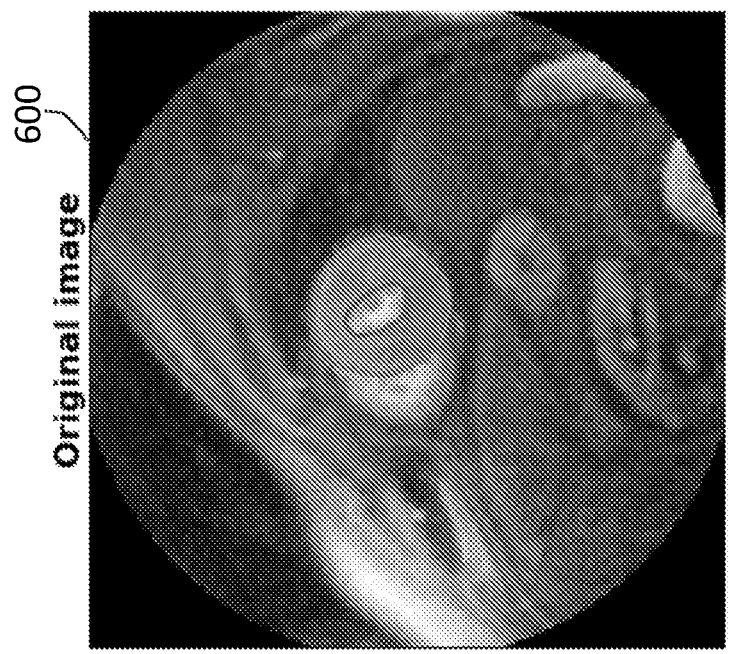
FIG. 6A is a first original frame of image data used as in examples of the techniques disclosed herein.

In a first embodiment of modeling myocardial tissue perfusion, a method according to this disclosure includes acquiring a plurality of original frames of magnetic resonance imaging (MRI) data representing images of a heart of a subject, as shown in FIG. 6 at 600. In some instances, and without limiting this disclosure, the methods include selecting original frames of image data after injecting a subject with gadolinium or other contrast material. While the disclosure herein is directed to myocardial applications, and the techniques involve acquiring original frames of MRI image data 600 of a left ventricle of the heart, these concepts are equally applicable to other kinds of MRI data as well.

In order to train a convolutional neural network 400 for use herein, the method includes developing a manually segmented set of ground truth frames 420 from the original frames 600 as a training set of data. The ground truth frames are known for accuracy in isolating, by segmenting or otherwise, the subject tissue under investigation, and they serve as a kind of goal image for the procedures described herein.

Figure 8:
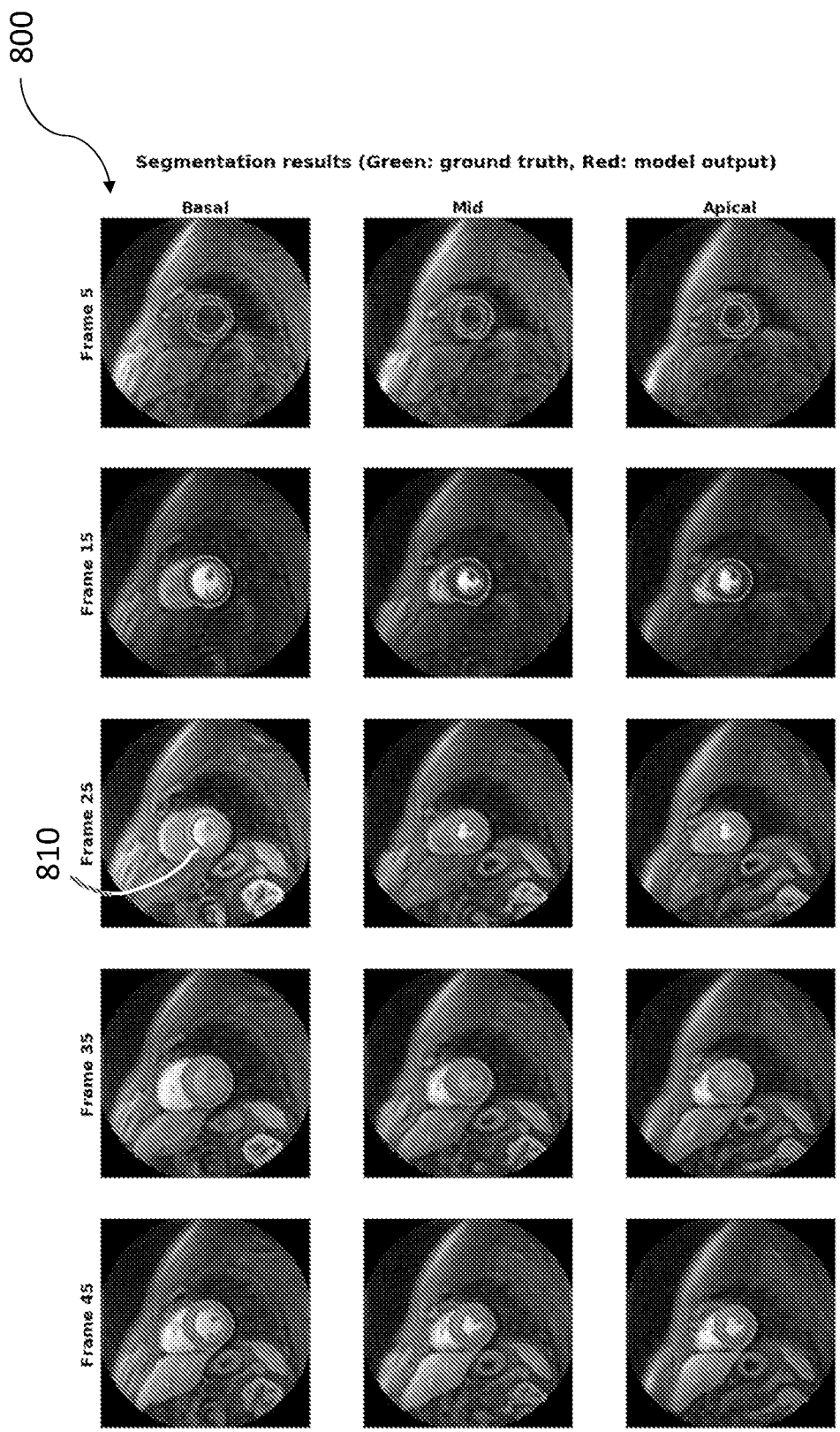
FIG. 8 is a first series of MRI images taken from the basal, mid-section, and apical section of the left ventricle and segmented for comparison with ground truth models as set forth herein.
Figure 9:
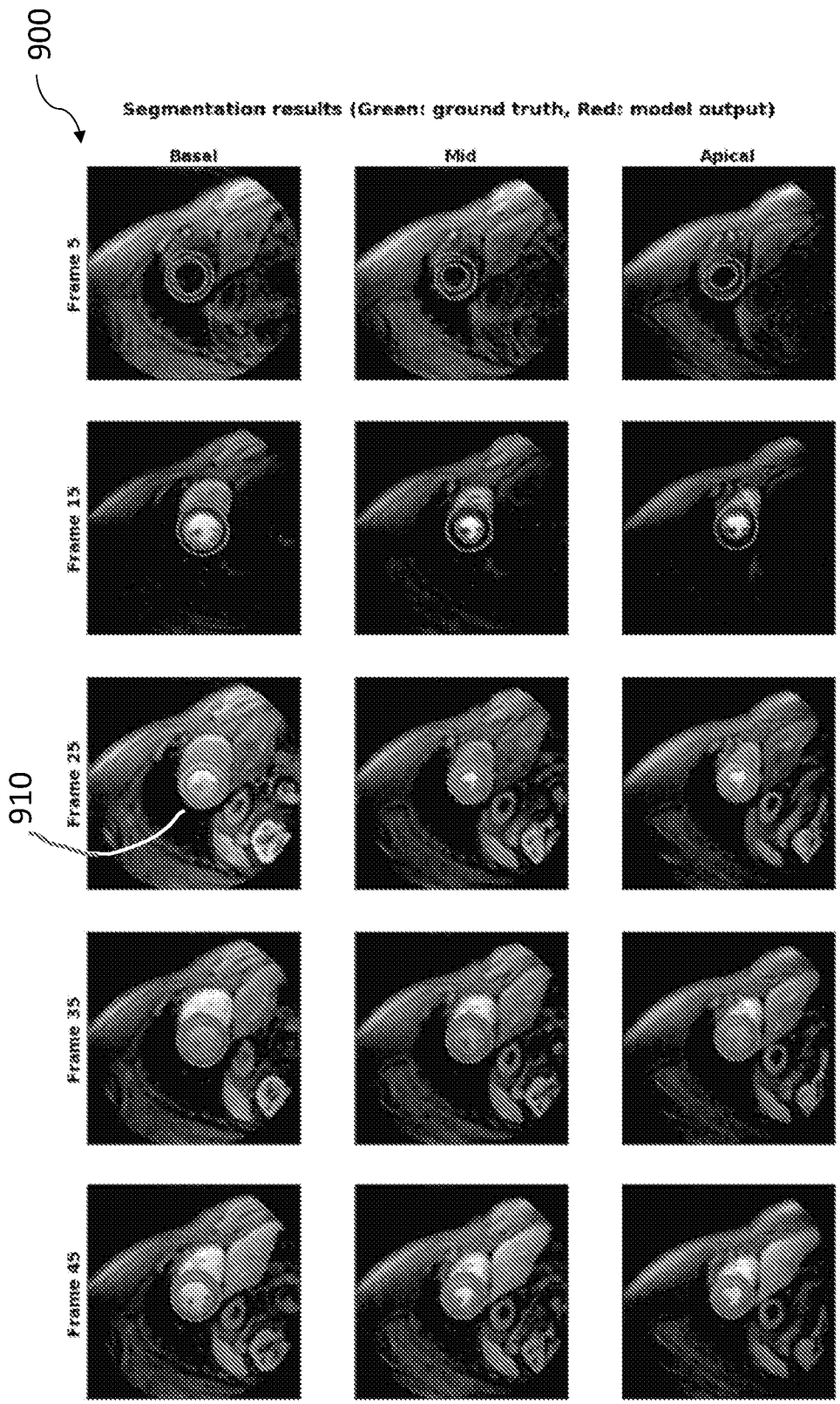
FIG. 9 is a second series of Mill images taken from the basal, mid-section, and apical section of the left ventricle and segmented for comparison with ground truth models as set forth herein.

Before using a CNN 400 for the purposes of this disclosure, practitioners often apply training augmentation techniques to the training set of the originals frame of MM data in preparation for training at least one convolutional neural network (CNN) to segment the training set of frames according to the ground truth frames as shown in FIG. 8 and FIG. 9. Training the CNN may be an iterative process by which multiple sets of training data are subject to the CNN operations for comparison to respective ground truth frames of image data. In one non-limiting embodiment, error data calculated by the CNN during the training phase is used as feedback to correct computer controlled algorithms and software implemented within the CNN.

Figure 7:
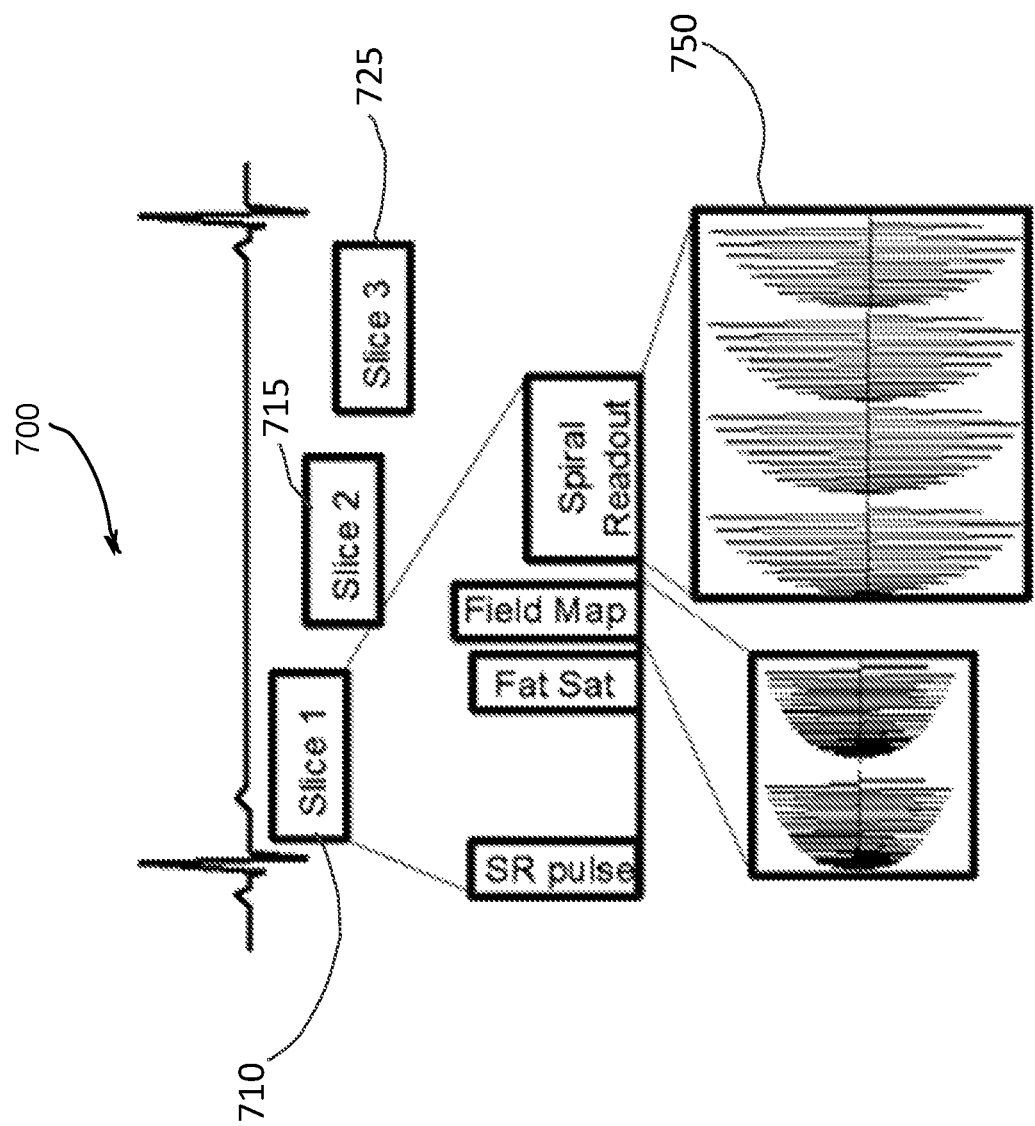
FIG. 7 is a schematic illustration of a spiral based data acquisition for perfusion images used in the methods and systems of the present disclosure.
Figure 10:
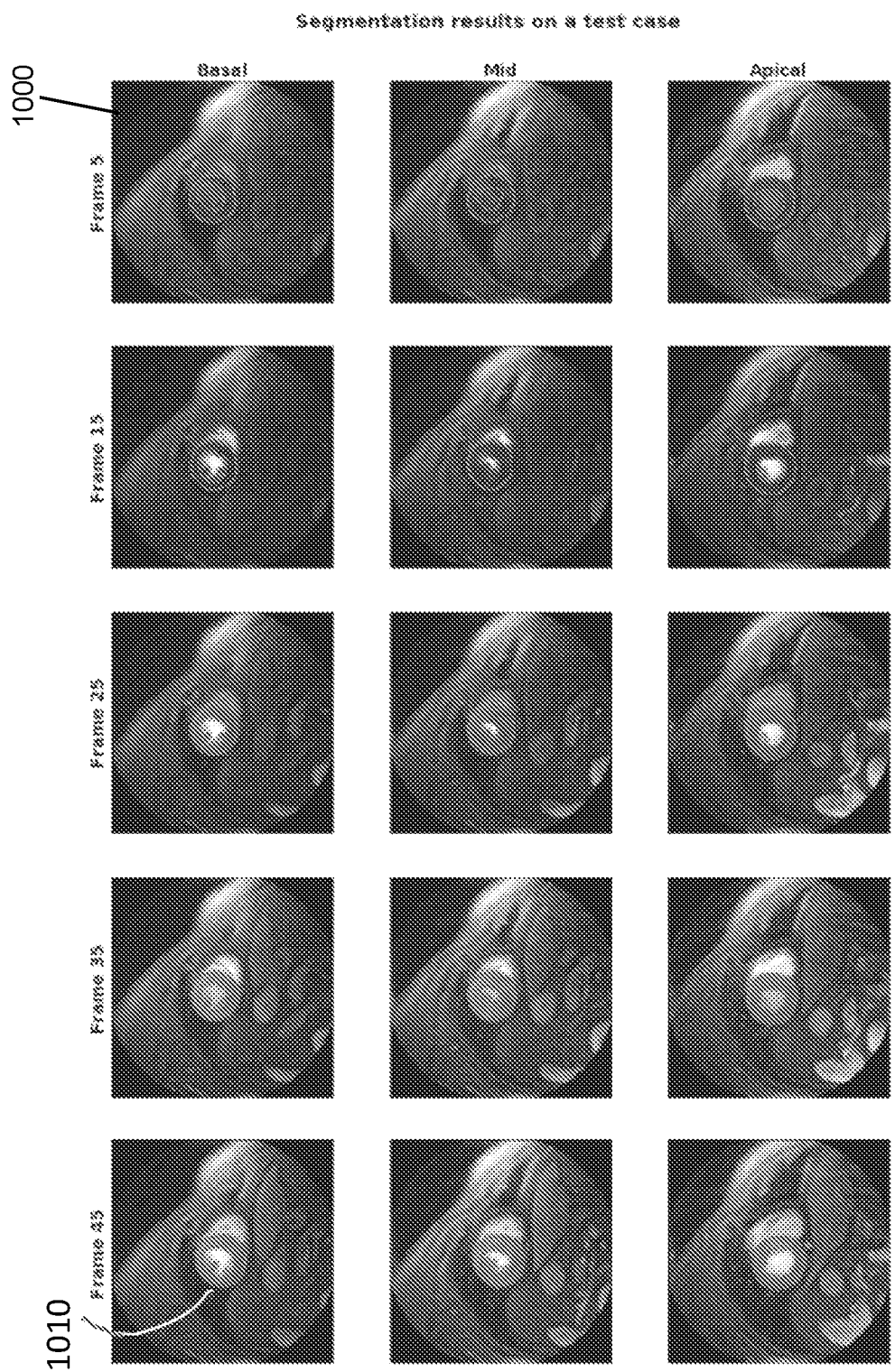
FIG. 10 is a third series of MRI images taken from the basal, mid-section, and apical section of the left ventricle of a test case and segmented as shown.

A trained CNN 400 may then be used for testing the CNN with a set of test images as input data 410. The test images may be acquired from databases of test data or may be real data collected from a subject for use with the CNN and typically include a plurality of original frames of Mill image data as shown in FIG. 7 at 700. Similar to the steps used in training, using the methods and systems of this disclosure, for test purposes or live diagnostic purposes, may include applying various pre-processing steps to the test images to create a corresponding set of input test frames used as image data input 410 to the CNN. The method continues by applying the respective input test frames to a trained CNN 400 for segmenting an endocardium layer and an epicardium layer as shown in FIGS. 8, 9, and 10 at 810, 910, and 1010 respectively, within the respective images of the input test frames. The CNN, therefore, produces segmented images, with the tissue under study clearly identified, that are useful in calculating myocardial blood flow into the myocardium from segmented images of the input test frames.

The pre-processing steps of this disclosure, described above as being optional steps for both training data and testing or live data, may include many image processing techniques that make the work of the CNN more efficient. Applying training augmentation may include steps including, but not limited to, applying at least one of b-spline based deformation (see FIG. 6B at 650) and affine transformation to the training set of frames. In this regard, applying b-spline deformation includes generating a random deformation field. Applying affine transformation includes applying at least one of translation, rotation, shear transformations, and combinations thereof, wherein the rotation is a random rotation between 0 and 360 degrees. Rotation is useful, in part, because convolution operation is translation-invariant but not rotation-invariant so that providing images at different angles can reduce model bias.

Pre-processing techniques are not limited to just training sets in the methods and systems of this disclosure. For example, pre-processing the test images (e.g., live recently acquired image data) may include rotating each of the test images a selected number of times, averaging respective output value probabilities for each pixel of each test image across all rotations, and calculating a respective input test image after applying a threshold comparison of averaged output value probabilities on a pixel by pixel basis. Other pre-processing steps may include unifying a matrix size and a spatial resolution of each of the input test images. Pre-processing for training data and test data (e.g., live data gathered from a test subject), may include, prior to applying the respective input test frames to the trained CNN, and for each pixel in the respective input images, subtracting a mean value of the entire set of pixels in a respective input test image or training image and dividing by a standard deviation of the entire set of pixels in the respective input test image or training image. Another pre-processing technique that has proven effective for preparing image data according to this disclosure includes converting the respective input test images (FIG. 5A at 500) to dilated convolution frames (FIG. 5B at 550) prior to using the test images as input image data 410 to the CNN 400.

The CNN set forth in this disclosure may also be referred to as a deep convolutional neural network (DCNN) configured as a U-Net. In one non-limiting example, the DCNN has at least four encoding layers and at least four decoding layers as shown by example in FIG. 4. In some embodiments, the method includes using a first encoding layer of the DCNN and producing a feature layer having 64 bit resolution as shown in FIG. 4 at 425. The CNN of this disclosure is configurable across numerous domains and achieves the goals related to tissue perfusion quantification for a variety of image types. For example, and without limiting this disclosure, each original frame of the MM imaging data, for testing data and training data, may include at least three slices (710, 715, 725) of the MM imaging data, wherein the respective slices represent basal, mid-ventricle, and apical views of the left ventricle (LV) as shown in FIGS. 8-10. Typically, but not exclusively, acquiring the original frames of data includes acquiring slices of MRI image data according to a spiral saturation recovery GRE sequence as illustrated in FIG. 7 at 750.

For preferred results in segmenting the myocardial tissue to study blood perfusion there through, the method may include training a pair of cascaded convolutional neural networks (CNNs), the pair including a first CNN for epicardium layer segmenting and a second CNN for endocardium layer segmenting. The respective CNNs may be trained and used similarly but adjusted for identifying their respective layers of tissue. When two CNNs are used, the method includes combining outputs of the two CNNs and forming an image feature map representing myocardial blood flow on a pixel by pixel basis.

Post-processing techniques may be applied to output images, including removing isolated pixel regions from the image feature map after combining the CNN outputs. Other quality control techniques within the scope of this disclosure include applying at least one motion correction algorithm to an output of the CNN. The motion correction algorithm includes, but is not limited to, applying deformable registration techniques to previously segmented images, wherein the deformable registration techniques comprise developing deformation fields with deformable registration between three-class label maps, wherein the label maps differentiate background pixels, myocardium pixels, and blood pool pixels.

After assembling output images in accordance with the CNNs of this disclosure, the methods further encompass calculating myocardial blood flow into the myocardium from segmented images with an arterial input function (AIF) calculated from the images with an automated workflow. The testing is evaluated according to Dice score, a commonly used technique to evaluate similarity in sets of data, and mean surface distance (MSD) against ground truth values.

All of the steps of each method disclosed herein may be implemented in a computerized system of modeling myocardial tissue perfusion a computer receiving MM image data, the computer comprising a processor and a memory storing computer implemented software. The software may be configured to implement a computerized method having steps of acquiring a plurality of original frames of magnetic resonance imaging (MM) data representing images of a heart of a subject, developing a manually segmented set of ground truth frames from the original frames; applying training augmentation techniques to a training set of the originals frame of MRI data; training at least one convolutional neural network (CNN) to segment the training set of frames according to the ground truth frames; testing the CNN with a set of test images from the plurality of original frames; pre-processing the test images to create a corresponding set of input test frames; applying the respective input test frames to a trained CNN for segmenting an endocardium layer and an epicardium layer within the respective images of the input test frames; and calculating myocardial blood flow into the myocardium from segmented images of the input test frames.

Without repeating every step discussed in regard to the method, this disclosure embodies software implemented on a computer to initiate all aspects of the above discussed methods.

CONCLUSION

The specific configurations, choice of materials and the size and shape of various elements can be varied according to particular design specifications or constraints requiring a system or method constructed according to the principles of the disclosed technology. Such changes are intended to be embraced within the scope of the disclosed technology. The presently disclosed embodiments, therefore, are considered in all respects to be illustrative and not restrictive. The patentable scope of certain embodiments of the disclosed technology is indicated by the appended claims, rather than the foregoing description.

What is claimed is:

1. A method of modeling myocardial tissue perfusion, comprising:
   acquiring a plurality of original frames of magnetic resonance imaging (MRI) data representing images of a heart of a subject;
   developing a manually segmented set of ground truth frames from the original frames;
   applying training augmentation techniques to a training set of the original frames;
   training at least one convolutional neural network (CNN) to segment the training set according to the ground truth frames;
   testing the CNN with a set of test images from the original frames by:
   pre-processing the test images to create a corresponding set of input test frames;
   applying the respective input test frames to a trained CNN for segmenting an endocardium layer and an epicardium layer within the respective images of the input test frames; and
   calculating myocardial blood flow into the myocardium from segmented images of the input test frames.

2. The method of claim 1, wherein applying training augmentation comprises applying at least one of b-spline based deformation and affine transformation to the training set.

3. The method of claim 2, wherein applying b-spline deformation comprises generating a random deformation field.

4. The method of claim 2, wherein applying affine transformation comprises applying at least one of translation, rotation, and shear transformations, wherein the rotation is a random rotation between 0 and 360 degrees.

5. The method of claim 1, wherein pre-processing the test images comprises rotating each of the test images a selected number of times, averaging respective output value probabilities for each pixel of each test image across all rotations, and calculating a respective input test image after applying a threshold comparison of averaged output value probabilities on a pixel by pixel basis.

6. The method according to claim 5, further comprising unifying a matrix size and a spatial resolution of each of the input test images.

7. The method according to claim 6, further comprising, prior to applying the input test frames to the trained CNN, for each pixel in the respective input test images, subtracting a mean value of the entire set of pixels in a respective input test image and dividing by a standard deviation of the entire set of pixels in the respective input test image.

8. The method according to claim 7, further comprising converting the respective input test images to dilated convolution frames prior to applying the input test frames to the trained CNN.

9. The method according to claim 1, wherein the CNN is a deep convolutional neural network (DCNN) configured as a U-Net having at least four encoding layers and at least four decoding layers.

10. The method according to claim 9, further comprising using a first encoding layer of the DCNN and producing a feature layer having 64 bit resolution.

11. The method according to claim 1, wherein each of the original frames comprises at least three slices of the MRI data, wherein the respective slices represent basal, mid-ventricle, and apical views of the left ventricle (LV).

12. The method according to claim 1, wherein acquiring the original frames comprises acquiring slices of MRI image data according to a spiral saturation recovery GRE sequence.

13. The method according to claim 1, further comprising training a pair of cascaded convolutional neural networks (CNNs), the pair comprising a first CNN for epicardium layer segmenting and a second CNN for endocardium layer segmenting.

14. The method according to claim 1, further comprising combining outputs of the two CNNs and forming an image feature map representing myocardial blood flow on a pixel by pixel basis.

15. The method according to claim 14, further comprising removing isolated pixel regions from the image feature map after combining the CNN outputs.

16. The method according to claim 1, comprising selecting the original frames after injecting the subject with gadolinium.

17. The method according to claim 1, comprising acquiring original frames of MRI image data of a left ventricle of the heart.

18. The method according to claim 1, further comprising calculating myocardial blood flow into the myocardium from segmented images with an arterial input function (AIF) calculated from the images with an automated workflow.

19. The method according to claim 1, further comprising applying a motion correction algorithm to an output of the CNN.

20. The method according to claim 19, wherein applying the motion correction algorithm comprises applying deformable registration techniques to the segmented images, wherein the deformable registration techniques comprise developing deformation fields with deformable registration between three-class label maps, wherein the label maps differentiate background pixels, myocardium pixels, and blood pool pixels.

21. The method according to claim 20, further comprising applying the deformation fields to the original images of MRI data.

22. The method according to claim 1, wherein the testing is evaluated according to DICE score and mean surface distance (MSD) against ground truth.

23. A computerized system of modeling myocardial tissue perfusion, comprising:
 a computer receiving MRI image data, the computer comprising a processor and a memory storing computer implemented software configured to implement a computerized method comprising the following steps:
 acquiring a plurality of original frames of magnetic resonance imaging (MRI) data representing images of a heart of a subject;
 developing a manually segmented set of ground truth frames from the original frames;
 applying training augmentation techniques to a training set of the originals frame of MRI data;
 training at least one convolutional neural network (CNN) to segment the training set of frames according to the ground truth frames;
 testing the CNN with a set of test images from the plurality of original frames;
 pre-processing the test images to create a corresponding set of input test frames;
 applying the respective input test frames to a trained CNN for segmenting an endocardium layer and an epicardium layer within the respective images of the input test frames; and
 calculating myocardial blood flow into the myocardium from segmented images of the input test frames.

* * * * *